(12) United States Patent
Aichinger et al.

(10) Patent No.: US 6,458,989 B1
(45) Date of Patent: Oct. 1, 2002

(54) METHOD FOR PRODUCING (METH) ACRYLIC ACID AND (METH)ACRYLIC ACID ESTERS

(75) Inventors: Heinrich Aichinger, Mannheim (DE); Hans Martan, Frankenthal (DE); Gerhard Nestler, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/646,126

(22) PCT Filed: Mar. 24, 1999

(86) PCT No.: PCT/EP99/01997

§ 371 (c)(1),
(2), (4) Date: Sep. 28, 2000

§ 102(e) Date: Sep. 28, 2000

(87) PCT Pub. No.: WO99/50221

PCT Pub. Date: Oct. 7, 1999

(30) Foreign Application Priority Data

Mar. 31, 1998 (DE) .......................... 198 14 449

(51) Int. Cl.⁷ .......................... C07C 67/48; C07C 51/42
(52) U.S. Cl. ...................... 560/218; 562/600
(58) Field of Search ........................... 562/600; 560/218

(56) References Cited

U.S. PATENT DOCUMENTS 3,844,903 A  10/1974  Willersinn et al.
6,207,022 B1 * 5/2001 Dockner et al. ............... 203/38

FOREIGN PATENT DOCUMENTS

| | | |
|---|---|---|
| DE | 1 950 750 | 7/1970 |
| DE | 2 164 767 | 7/1972 |
| EP | 0 551 111 | 7/1993 |
| EP | 0 727 408 | * 8/1996 |
| FR | 0727408 | * 8/1996 |
| GB | 1120284 | 7/1968 |
| JP | 71 06 886 | 2/1971 |

* cited by examiner

*Primary Examiner*—Mukund J. Shah
*Assistant Examiner*—Zachary Tucker
(74) *Attorney, Agent, or Firm*—Oblon, Spivak, McClelland, Maier & Neustadt, P.C.

(57) ABSTRACT

A process for preparing pure (meth)acrylic acid or a (meth) acrylate starting from a crude (meth)acrylic acid, which comprises the following stages:

A: treating the crude (meth)acrylic acid with at least one compound which is able to remove aldehydes, to give an aldehyde-free crude (meth)acrylic acid;

B: subjecting the aldehyde-free crude (meth)acrylic acid to imprecise distillation, to give a low-boiling fraction comprising (meth)acrylic acid and acetic acid and a high-boiling fraction comprising (meth)acrylic acid and high boilers;

C: isolating a pure (meth)acrylic acid from the high-boiling fraction and, if desired, D: esterifying the low-boiling fraction comprising (meth) acrylic acid and acetic acid that is obtained in stage B by means of one or more alkanols, to give an esterification mixture comprising one or more (meth) acrylates, one or more acetic esters, and one or more alkanols.

14 Claims, No Drawings

METHOD FOR PRODUCING (METH) ACRYLIC ACID AND (METH)ACRYLIC ACID ESTERS

The present invention relates to a process for preparing pure (meth)acrylic acid from a crude (meth)acrylic acid, in which a crude (meth)acrylic acid which is of low water content and in addition to (meth)acrylic acid essentially comprises acetic acid and possibly aldehydes is treated with a compound which is able to remove aldehydes, and the aldehyde-free crude (meth)acrylic acid thus obtained is subjected to imprecise distillation, and then the (meth) acrylic acid obtained as the bottom product, which is substantially free from acetic acid, is separated from the other high boilers to give pure (meth)acrylic acid. Preferably, the low-boiling fraction obtained in the imprecise distillation, which consists predominantly of (meth)acrylic acid and acetic acid, is esterified with alkanols to give (meth) acrylates.

By the term "crude (meth)acrylic acid" used in accordance with the invention is meant a mixture comprising (meth)acrylic acid that is prepared by catalytic gas-phase oxidation of $C_3$ and/or $C_4$ precursors, absorption in a high-boiling solvent, desorption of the low boilers, and distillative separation from the solvent, comprises at least 90% by weight of (meth)acrylic acid, and is substantially free from water.

By "pure (meth)acrylic acid" is meant an aldehyde-free (meth)acrylic acid have a purity of at least 99.7% by weight, which is suitable for preparing high molecular mass addition polymers.

The term (meth)acrylic acid or (meth)acrylate used in the context of the present invention stands for acrylic and methacrylic acid or, respectively, their esters.

By virtue of its highly reactive double bond and the acid function, (meth)acrylic acid forms a valuable monomer for preparing addition polymers—for example, for aqueous polymer dispersions suitable as adhesives.

One way to obtain acrylic acid is by gas-phase oxidation of propylene and/or acrolein with oxygen, or oxygen-containing gases, in the presence of catalysts at elevated temperature, preferably with dilution of the reactants with inert gases and/or steam owing to the high heat of reaction.

Catalysts employed in this reaction are generally multicomponent systems of oxide type, based, for example, on oxides of molybdenum, of chromium, of vanadium or of tellurium.

However, this process produces not pure acrylic acid but rather a gas mixture which in addition to acrylic acid comprises secondary components—essentially unreacted acrolein and/or propylene, steam, oxides of carbon, nitrogen, oxygen, acetic acid, formaldehyde, benzaldehyde, furfurals, and maleic anhydride—from which the acrylic acid must subsequently be separated off.

Methacrylic acid can be prepared analogously starting from the corresponding $C_4$ compounds.

(Meth)acrylic contaminated in this way (crude (meth) acrylic acid) cannot be used further directly for, say, the preparation of high molecular mass polymers but instead must be subjected to a laborious purification procedure. In general, this requires a plurality of distillation steps in order to attain the necessary purity of at least approximately 99.7% (pure (meth)acrylic acid) (see Kirk-Othmer, Encycl. of Techn. Chem., 4th Ed., pp. 299–300).

Aldehydes, which have an adverse effect on the polymerisation behavior of the (meth)acrylic acid, are removed generally by treatment with primary amines, hydrazines or aminoguanidine and subsequent distillation. In this case, said compounds which are able to remove aldehydes are added prior to the distillation.

Owing to the small differences in boiling point and the generally high tendency of (meth)acrylic acid to undergo polymerization on thermal exposure, the distillative separation of the acetic acid from the (meth)acrylic acid constitutes an extremely difficult purification step, which entails a high level of technical effort, and losses in yield.

According to DE-A 19 50 750 (see col. 2, lines 31–53), a distillation column having at least 55 trays and a reflux ratio of 15 is required to separate acrylic acid from acetic acid to some extent.

In order to solve this problem, a variety of proposals have been made to date:

The separation of acrylic acid from, for example, the reaction mixture from the oxidation of propylene, which consists essentially of acrylic acid, acetic acid, aldehydes and water, by means of an azeotropic distillation, in which the acetic acid and the water are distilled off with an entrainer; entrainers employed are, for example, esters, alcohols, ketones, aromatics, alkanes, or mixtures thereof (see DE-A 19 50 750, GB-B 1 120 284 and EP-A 0 551 111).

JA 71-06 886 proposes solving this problem by an extractive distillation with formamides and/or acetamides.

The processes described above are technically complex. Furthermore, according to these documents, the low-boiling fraction obtained in the above processes, which consists predominantly of acetic acid, acrylic acid, aldehydes, water and possibly solvents, is generally discarded.

EP-A 0 727 408 proposes the use of the low-boiling fraction obtained in the distillative recovery of pure acrylic acid for preparing alkyl acetates. A prerequisite for this is extremely precise separation of acetic from acrylic acid, which entails great problems and a high level of technical effort, and requires laborious purification of the ester. The process described therein is, therefore, comparatively uneconomic.

DE-A 21 64 767 proposes a distillative separation in which an acrylic acid content from 10 to 70% is established in the low-boiling fraction. In this way, it is said, the customary polymerization problems are largely avoided. The mixture of acetic and acrylic acid is passed to the workup stage of the aqueous crude acrylic acid. This process can only be carried out when an independent crude acrylic acid preparation stage, or an apparatus for working up aqueous acrylic acid solutions, is present, which is only seldom the case.

The preparation of (meth)acrylates by acid-catalyzed esterification of (meth)acrylic acid with one or more alkanols is also known from the prior art. Of such esterification reactions it is known, very generally, that they are equilibrium reactions and, consequently, that the presence of water in the reaction equilibrium prevents economic conversion rates. Accordingly, the (meth)acrylic acid employed is generally substantially free from water, and the water of reaction produced in the esterification is removed by distillation, with or without the aid of an entrainer.

As already mentioned at the outset, the preparation of (meth)acrylic acid by oxidation starting from the corresponding $C_3/C_4$ precursors also produces considerable amounts of acetic acid (from about 0.5 to 10% by weight). Owing to the small differences in boiling point and the high tendency of the (meth)acrylic acid to undergo polymerization on thermal exposure, distillative separation of the abovementioned byproducts is difficult and expensive (U.S. Pat. No. 3,844,903, DE-A 2 164 767).

When (meth)acrylic acid containing acetic acid is esterified with alkanols the acetic acid too is esterified, and the formation of acetic esters entails additional separation effort and a loss of alkanol. Another point to note here is that the distillative separation of the acetic ester from the esterification mixture, especially its separation from unreacted alkanol, is hindered by the formation of binary azeotropes. In the case of butanol, for example, the butanol/butyl acetate azeotrope boils at 115.8° C. (57% butanol), with butanol boiling at 117.4° C. and butyl acetate at 125.6° C.

Since the acetic esters are of relatively high volatility and are not polymerizable, there is a general need when preparing polymers for (meth)acrylic esters of high purity, i.e., being free as far as possible—that is substantially free—from acetic esters. The acetic ester remaining, say, in a coating dispersion or in an adhesive would in fact be the origin, inter alia, of a severe odor nuisance. Laborious removal (deodorization) of the acetic ester would be required.

As can be perceived from the above text, a fundamental problem in (meth)acrylate preparation is that of excessive consumption of alcohols, which is disadvantageous both economically and environmentally.

In the light of the above prior art, it is an object of the present invention to provide a process for preparing pure (meth)acrylic acid that is easy to carry out industrially and in which the other products of value obtained in the preparation of pure (meth)acrylic acid can likewise be used advantageously if desired.

We have found that this object is achieved by a process for preparing pure (meth)acrylic acid starting from a crude (meth)acrylic acid, which comprises the following stages:

A: treating the crude (meth)acrylic acid with at least one compound which is able to remove aldehydes, to give an aldehyde-free crude (meth)acrylic acid;

B: subjecting the aldehyde-free crude (meth)acrylic acid to imprecise distillation, to give a low-boiling fraction comprising (meth)acrylic acid and acetic acid and a high-boiling fraction comprising (meth)acrylic acid and high boilers; and C: isolating a pure (meth)acrylic acid from the high-boiling fraction.

The invention provides in particular a process, as defined above, in which the low-boiling fraction comprising (meth)acrylic acid and acetic acid that is obtained in stage B is subjected to an esterification in accordance with stage D:

D: esterifying the low-boiling fraction comprising (meth)acrylic acid and acetic acid that is obtained in stage B by means of one or more alkanols, to give an esterification mixture comprising one or more (meth)acrylates, one or more acetic esters, and one or more alkanols.

In this process, the detailed procedure is as follows:

A crude (meth)acrylic acid obtained by gas-phase oxidation and subsequent workup as mentioned in the introduction of the present document, which essentially comprises, other than (meth)acrylic acid, from about 0.2 to about 10% by weight of acetic acid, from about 0.05 to 1% by weight of aldehydes and from about 0.05 to 5% by weight of water, is first of all treated with a compound which is able to remove aldehydes, to give an aldehyde-free or essentially aldehyde-free-crude (meth)acrylic acid. The aldehyde content of the aldehyde-free crude (meth)acrylic acid is generally not more than 10 ppm, preferably not more than 5 ppm.

For this purpose, the crude (meth)acrylic acid is generally subjected at from approximately 20 to approximately 40° C. to treatment with a compound which is able to remove aldehydes, preferably an amino-functional compound. Particular such compounds which may be mentioned are aminoguanidine hydrogen carbonate, hydrazine, and adipic dihydrazide, and also mixtures of two or more of these.

The treatment described above generally lasts for 2 to 20 hours.

Subsequently, the aldehyde-free crude (meth)acrylic acid is subjected to imprecise distillation, whose primary purpose is to separate off the acetic acid still present in the crude (meth)acrylic acid. In the course of this imprecise distillation, a low-boiling fraction is obtained which generally comprises at least 70% by weight of (meth)acrylic acid.

The term "imprecise distillation" as used in accordance with the invention refers to a distillation in which a mixture comprising two or more components is distilled under conditions such that the sole products are a first component (in this case (meth)acrylic acid), which is obtained in high purity, and the other component(s), which is (are) obtained as a mixture with the first component and any further constituents of the mixture (in this case acetic acid and (meth)acrylic acid).

The imprecise distillation is carried out in a distillation unit familiar to the skilled worker. In general, a column with from 20 to 50 trays, preferably bubble-cap, sieve and dual-flow trays, or a corresponding packed column is employed. The bottom (liquid-phase) temperature during the distillation is generally from approximately 50 to approximately 130° C., preferably from approximately 60 to approximately 100° C., with operation taking place at a column-top pressure of from about 20 to about 200 mbar and with a reflux ratio of from about 1 to about 10.

Preference is given to operation at a temperature from approximately 60 to approximately 100° C., a column-top pressure from about 20 to about 200 mbar and a reflux ratio of from 1 to 10, using a column with dual-flow trays.

The column is stabilized by adding a polymerization inhibitor to the reflux: it is preferred to add phenothiazine, a phenolic compound, an N-O compound, copper salts, sulfonic salts, or a mixture of two or more of these, and also preferably phenothiazine or hydroquinone, a mixture of phenothiazine and hydroquinone, hydroquinone monomethyl ether, p-nitrosophenol, nitrosodiethylaniline or tetramethyl-piperidine-1-oxyls, as are described in DE-A 16 18 141.

With further preference, the column is stabilized by using sulfonic salts of phenothiazine as a polymerisation inhibitor. These compounds can be obtained in a simple manner by reacting phenothiazine with corresponding sulfonic acids in accordance with EP-A 0 775 686. Particular preference is given to the use of thiodiphenylammonium alkylbenzenesulfonates, especially to those with $C_6$ to $C_{20}$ alkyl groups.

Consequently, the present invention also provides for the use of a sulfonic salt of phenothiazine as a polymerization inhibitor for (meth)acrylic acid.

The evaporator or condenser employed is likewise an apparatus known to the skilled worker, preference being given to the use of a Robert evaporator or a quench condenser, which is operated at from approximately 20 to approximately 40° C.

In stage B there is produced not only the low-boiling fraction comprising (meth)acrylic acid and acetic acid, which has already been discussed, but also a high-boiling fraction comprising a (meth)acrylic acid and high boilers. This fraction, which is obtained as the bottom product, is subjected to a separation stage C, in which pure (meth)acrylic acid is obtained by distillation in a manner familiar to the skilled worker.

In this stage, in the separation of the (meth)acrylic acid by distillation, pure (meth)acrylic acid is obtained as the top product. No great separation effort is made in this step, so that the (meth)acrylic acid can preferably be simply "topped".

By "topping" is meant in accordance with the invention a distillation in which the product is drawn off directly from the top in vapor form and is subsequently condensed without coming into contact with any reflux. The column used in this procedure has virtually no internals providing for effective separation.

This "topping" operation takes place by way of a splash guard, with the bottom temperature being from approximately 50 to approximately 120° C., preferably from approximately 60 to 100° C., and the pressure being adjusted accordingly depending on the bottom temperature used.

The pure (meth)acrylic acid is condensed with the aid of a quench at from approximately 20 to approximately 30° C.

Preferably, the splash guard is loaded with pure (meth) acrylic acid which is stabilized with from 150 to 200 ppm of stabilizer, such as hydroquinone monomethyl ether.

The purity of the resulting pure (meth)acrylic acid is from about 99.7 to about 99.9%, the acetic acid content from about 100 to 800 ppm, and the furfural content not more than 1 ppm.

The low-boiling fraction obtained in stage B which comprises predominantly (meth)acrylic acid and acetic acid is aldehyde-free or essentially aldehyde-free and consists essentially of about 70% by weight, preferably from about 80 to about 95% by weight (meth)acrylic acid, from about 3 to about 15% by weight acetic acid and from about 0.5 to about 10% by weight water. In one preferred embodiment of the process of the invention, the low-boiling fraction can be conventionally esterified with one or more alkanols by a prior art process as described, for example, in DE-A 195 47 485 and the prior art cited therein, DE-A 195 47 485 being incorporated in its entirety into the context of the present document by reference.

In that case, the low-boiling fraction obtained in stage (B) is esterified directly with a $C_1$–$C_{12}$-, preferably a $C_1$–$C_{10}$- and, in particular, a $C_4$–$C_8$-alkanol, the precise esterification conditions being dependent on the alkanol used.

Preferred alkanols are:
Methanol, ethanol, isopropanol, n-propanol, n-butanol, isobutanol, octanol, and 2-ethylhexanol, preferably n-butanol, isobutanol and 2-ethylhexanol.

Typical conditions under which the esterification can take place are as follows:
Ratio alkanol:(meth)acrylic acid:
1:0.7–1.2 (molar)
Catalyst:
sulfuric acid or a sulfonic acid, such as p-toluene sulfonic acid
Amount of catalyst:
About 0.1–10% by weight, preferably about 0.5–5% by weight, based in each case on the starting materials
Stabilizer:
Phenothiazine, hydroquinone, hydroquinone monomethyl ether, phenylenediamine and, if desired, air
Amount of stabilizer:
About 100—about 50,000 ppm, preferably about 500—about 2000 ppm, based in each case on (meth)acrylic acid.
Reaction temperature:
Approximately 80–160° C., preferably approximately 90–130° C.

Pressure during the reaction:
From 0.5 to 1.5 bar, preferably atmospheric pressure
Reaction period:
From about 1 to about 10 hours, preferably from about 1 to 6 hours.

If desired, an entrainer such as cyclohexane or toluene, for example, can be used to remove the water which is produced during the esterification.

The esterification per se can be conducted at atmospheric, superatmospheric or subatmospheric pressure and either continuously or batchwise, with preference being given to a continuous regime encompassing the overall process, i.e., a continuous implementation of stages A to F as elucidated herein.

Since in accordance with the invention the low-boiling fraction obtained in stage B is esterified, the result is an esterification mixture comprising not only the desired (meth) acrylate(s) but also the corresponding acetic ester(s). In addition, the esterification mixture comprises the alkanol or alkanols.

The (meth)acrylates are isolated in a conventional manner. In general, here, first the catalyst and the unreacted (meth)acrylic acid are removed by washing and then the esterification mixture is separated, preferably by distillation.

This separation produces, on the one hand, the one or more (meth)acrylates (in the liquid phase) and, on the other hand, a separation mixture which comprises the acetic ester(s) and one or more alkanols (stage E). This separation mixture is preferably hydrolyzed in a further stage F to give a hydrolysis mixture which comprises the one or more alkanols and acetic salts. The alkanol, in turn, can subsequently be separated off from this hydrolysis mixture.

The procedure here in detail is preferably as follows:
The esterification mixture obtained is preferably washed with aqueous alkali metal hydroxide solution, preferably from about 1 to about 10% strength by weight sodium hydroxide solution and water, in order to separate off the acid (catalyst and unreacted carboxylic acids). In a customary distillation unit, a low-boiling fraction which comprises, inter alia, the acetic ester and unreacted alkanol, and a bottom product which comprises the major amount of the (meth)acrylate, are obtained from the substantially acid-free esterification mixture.

In general this is done using a distillation column having from about 40 to about 60 trays, preferably bubble-cap, sieve or dual-flow trays, or a corresponding packed column.

The bottom temperature in this case, which is dependent on the alkanol employed, is from approximately 50 to approximately 150° C., with the pressure being established correspondingly. The reflux ratio is generally from about 3 to about 10. The column is stabilized by way of the reflux by adding from about 50 to about 500 ppm of inhibitor, preferably phenothiazine, hydroquinone, hydroquinone monomethyl ether, phenylenediamine, nitroso compounds, or mixtures thereof.

The amount of the low-boiling fraction removed in this case depends critically on the concentration of the acetic ester in the esterification mixture, and is generally from about 5 to about 30% of the feed.

The low-boiling fraction obtained, which, as mentioned, consists predominantly of alkanol (from about 10 to about 50% by weight), acetic ester (from about 10 to about 80% by weight) and (meth)acrylate (from about 1 to about 30% by weight), is hydrolyzed at boiling temperature with a from 5 to 40% strength by weight alkali metal hydroxide solution over a period of about 1 to about 10 hours.

Here, the low-boiling fraction can if desired be separated in a further distillation step into a top product, consisting predominantly of alkanol and acetic ester, which is then hydrolyzed, and a bottom product, which consists essentially of (meth)acrylate.

The resultant (meth)acrylate is preferably supplied to the distillative workup of the esterification mixture.

The reaction with alkali metal hydroxide solution (hydrolysis) can be carried out continuously or batchwise, under atmospheric, superatmospheric or subatmospheric pressure. It is preferably carried out using a stirred reactor or a tube reactor.

The separation of the alkanol from the hydrolysis mixture which is obtained depends on the nature of the alkanol; that is, on its solubility in water. Water-insoluble alkanols form a second phase and can be separated off with ease. Water-soluble alkanols are separated off, for example, by distillation or by stripping with air or steam. Preferably, the alkanols obtained are then in turn supplied to the esterification. Distillative separation or stripping can take place, for example, in a heatable stirred reactor with a column mounted on it. The energy can be supplied conventionally (jacket heating, coil heating, circulation heating, etc.).

The stripping of the alkanol in a stripping column can take place conventionally. For example, the hot (from approximately 40 to approximately 80° C.) hydrolysis solution can be fed in at the top of a column and stripped in countercurrent with air (from about 1 to about 20 $m^3/m^3$) or steam (from about 0.1 to about 10 $t/m^3$). The alkanol can be condensed from the stripping gas with a conventional condenser, such as a tube bundle heat exchanger or plate-type heat exchanger.

The alkanol can then be resupplied to the esterification of stage D.

The process of the invention has the following advantages:

1. The (meth)acrylic acid obtained is extremely pure, i.e., free or essentially free from aldehydes and substantially free from acetic acid.
2. The distillative separation of the acetic acid takes place without polymerization problems. This is surprising since the addition of amino-functional compounds is known to reduce sharply the stability of (meth)acrylic acid.
3. The mixture of (meth)acrylic acid and acetic acid obtained as the low-boiling fraction in the distillative separation of (meth)acrylic acid and acetic acid is put to an economically rational use.
4. The (meth)acrylates obtained from the fraction containing acetic acid are already free from aldehydes and therefore need not be additionally purified.
5. The hydrolysis of the separation mixture defined herein allows recovery of the alkanol bound in the acetic ester. The separation of the alkanol from the acetic ester, which would otherwise be necessary for economic reasons but is difficult owing to the formation of binary azeotropes, can be omitted as a result.

The present invention will now be elucidated with reference to an example:

EXAMPLE

In a hold-up container, crude acrylic acid prepared by propene oxidation in accordance with DE-A 43 08 087 and comprising, in addition to acrylic acid, essentially 0.1% by weight diacrylic acid, 0.2% by weight acetic acid, 0.04% by weight propionic acid, 0.05% by weight maleic acid, 0.06% by weight furfural, 0.01% by weight benzaldehyde, 0.08% by weight water and 500 ppm phenothiazine, is admixed with 0.2% by weight of aminoguanidine hydrogen carbonate and mixed by being pumped in circulation at 23° C. for six hours.

The resultant mixture was supplied to a distillation unit which consisted of a dual-flow column with 25 trays, a Robert evaporator and a quench condenser. The feed (11 $m^3/h$) was added at tray 22, the bottom temperature was 87° C. and the column-top temperature was 68° C. at 60 mbar. The quench condenser was operated at 30° C. with a circulation flow of 400 $m^3/h$.

The column was stabilized with thiodiphenylammonium dodecylbenzenesulfonate, which was prepared by reacting phenothiazine (600 ppm) with dodecylbenzenesulfonic acid (1000 ppm) in the quench liquid, said quench liquid being applied as reflux to the topmost column tray (2 $m^3/h$). The quench liquid was stabilized with 300 ppm phenothiazine and, in addition to acrylic acid, contained essentially 1.9% by weight acetic acid and 2.1% by weight water. 1 $m^3/h$ was removed.

The distillation column was operated for 30 days with no problem.

The bottom liquid, which consisted predominantly of acrylic acid, was passed to the Robert evaporator of a second distillation unit, whose column was fitted only with a splash guard and likewise had a quench condenser (400 $m^3/h$ circulation flow, T=22° C.). The quench liquid was stabilized with 200 ppm of hydroquinone monomethyl ether.

The bottom temperature was 73° C. and the column-top temperature 73° C. at 60 mbar. The condensate (9.3 $m^3/h$) had essentially the following composition:

99.8% by weight acrylic acid
0.04% by weight acetic acid
0.04% by weight propionic acid and
0.03% by weight water.

Aldehydes were no longer detectable by gas chromatography.

A cascade of stirred vessels, consisting of three stirred reactors each with a capacity of 1 l and equipped with column, condenser and phase separation vessel, was charged with 500 g of the discharge from the quench, which consisted essentially of 95.9% by weight acrylic acid, 1.9% by weight acetic acid and 2.1% by weight water, and with 550 g of butanol, 0.1% by weight phenothiazine and 15 g of sulfuric acid per hour.

The reaction temperature in the stirred reactors was 103° C., 117° C. and 122° C. respectively, and the pressure was 700 mbar.

At the top of the column, a mixture of water, butanol, butyl acetate and butyl acrylate was obtained which separated into an aqueous phase and an organic phase; after the addition of 300 ppm of phenothiazine, the organic phase was supplied as reflux to the column.

The reactor discharge (930 g/h) was cooled to 30° C., the unreacted acrylic acid and the catalyst were neutralized with 5% strength sodium hydroxide solution, washing was carried out with water, after which the mixture was distilled in a column with 60 sieve trays.

The feed of the column took place at the fifth tray, the bottom temperature was 109° C., and the column-top temperature was 86° C. at 160 mbar. At the top of the column, 910 g/h of distillate were obtained, which separated into an organic phase and a water phase. Following the addition of 300 ppm of phenothiazine, 806 g/h of the organic phase were applied as a reflux to the topmost tray of the column again, and 92 g/h were removed.

The organic phase of the distillate contained essentially 20% by weight butyl acetate, 36.6% by weight butanol, and 38.0% by weight butyl acrylate. In a further sieve-tray column (30 trays), the butyl acrylate from the product run off from the bottom of the column was isolated (738 g/h) as column-top product. The bottom temperature was 108° C., the column-top temperature 80° C. at 100 mbar, and the reflux ratio was 0.6.

The butyl acrylate recovered had a purity of 99.8% by weight, contained 130 ppm of butyl acetate, and was aldehyde-free.

A mixture of 1000 g of the organic phase of the distillate was heated under reflux for two hours with 30% strength sodium hydroxide solution (2000 g) in a stirred reactor. After the end of the hydrolysis reaction, the butanol formed was separated off from the reactor by distillation via a column (10 bubble-cap trays) under subatmospheric pressure (500 mbar). The condensate separated into a water phase and an organic phase (706 g). The organic phase contained about 84% by weight butanol and, mixed with fresh butanol, can be passed back directly again to the esterification.

In this way it was possible to recover 79% of the theoretical amount of butanol.

We claim:

1. A process for preparing pure (meth)acrylic acid starting from a crude (meth)acrylic acid, which comprises the following stages:

A: treating the crude (meth)acrylic acid with at least one compound which is able to remove aldehydes, to give an aldehyde-free crude (meth)acrylic acid which contains acetic acid and high boilers;

B: subjecting the aldehyde-free crude (meth)acrylic acid to imprecise distillation, to give a low-boiling fraction comprising at least 70% by weight of (meth)acrylic acid and also acetic acid and a high-boiling fraction comprising (meth)acrylic acid and high boilers;

C: isolating a pure (meth)acrylic acid from the high-boiling fraction, and

D: esterifying the low-boiling fraction comprising (meth)acrylic acid and acetic acid that is obtained in stage B by means of one or more alkanols, to give an esterification mixture comprising one or more (meth)acrylates, one or more acetic esters, and one or more alkanols.

2. The process as claimed in claim 1, wherein the compound which is able to remove aldehydes is an aminofunctional compound.

3. The process as claimed in claim 1, wherein stage B is conducted in a dual-flow column at a temperature in the range from 60 to 100° C. and at a column-top pressure of from 20 to 200 mbar and with a reflux ratio of from 1 to 10.

4. The process as claimed in claim 1, wherein the pure (meth)acrylic acid from the high-boiling fraction is separated off by topping.

5. The process as claimed in claim 1, further comprising stage E:

E. separating the esterification mixture to give one or more (meth)acrylates and a separation mixture which comprises one or more acetic esters and one or more alkanols.

6. The process as claimed in claim 5, which comprises an additional stage F:

F: hydrolyzing the separation mixture to give a hydrolysis mixture which comprises one or more alkanols and acetic salts.

7. The process as claimed in claim 6, wherein the alkanol or alkanols is or are separated off from the hydrolysis mixture and passed back to the esterification of stage D.

8. The process as claimed in claim 1, wherein in stage B a sulfonic salt of phenothiazine is used as a polymerization inhibitor for (meth)acrylic acid.

9. The process as claimed in claim 2, wherein stage B is conducted in a dual-flow column at a temperature in the range from 60 to 100° C. and at a column-top pressure of from 20 to 200 mbar and with a reflux ratio of from 1 to 10.

10. The process as claimed in claim 9, wherein the pure (meth)acrylic acid from the high-boiling fraction is separated off by topping.

11. The process as claimed in claim 10, which comprises a further stage E:

E: separating the esterification mixture to give one or more (meth)acrylates and a separation mixture which comprises one or more acetic esters and one or more alkanols.

12. The process as claimed in claim 11, which comprises an additional stage F:

F: hydrolyzing the separation mixture to give a hydrolysis mixture which comprises one or more alkanols and acetic salts.

13. The process as claimed in claim 12, wherein the alkanol or alkanols is or are separated off from the hydrolysis mixture and passed back to the esterification of stage D.

14. The process as claimed in 13, wherein in stage B a sulfonic salt of phenothiazine is used as a polymerization inhibitor for (meth)acrylic acid.

* * * * *